(12) United States Patent
Kupfer et al.

(10) Patent No.: US 7,680,614 B2
(45) Date of Patent: Mar. 16, 2010

(54) METHOD FOR DETERMINING THE HUMIDITY AND DENSITY OF A DIELECTRIC MATERIAL

(75) Inventors: Klaus Kupfer, Weimar (DE); Eberhard Trinks, Weimar (DE)

(73) Assignee: Sartorius AG, Goettingen (DE)

( * ) Notice: Subject to any disclaimer, the term of this patent is extended or adjusted under 35 U.S.C. 154(b) by 480 days.

(21) Appl. No.: 10/577,595

(22) PCT Filed: Oct. 27, 2004

(86) PCT No.: PCT/DE2004/002390

§ 371 (c)(1),
(2), (4) Date: Sep. 14, 2007

(87) PCT Pub. No.: WO2005/045411

PCT Pub. Date: May 19, 2005

(65) Prior Publication Data

US 2008/0234958 A1 Sep. 25, 2008

(30) Foreign Application Priority Data

Oct. 27, 2003 (DE) .............................. 103 50 224

(51) Int. Cl.
*G01R 23/00* (2006.01)
(52) U.S. Cl. ...................... 702/75; 702/76; 702/137
(58) Field of Classification Search ................ 702/75, 702/76, 137
See application file for complete search history.

(56) References Cited

U.S. PATENT DOCUMENTS

| 3,732,846 A | * | 5/1973 | Lukaszek .................... 118/668 |
|---|---|---|---|
| 4,058,766 A | | 11/1977 | Vogel et al. |
| 4,611,164 A | * | 9/1986 | Mitsuyoshi et al. ...... 324/76.19 |
| 5,397,993 A | * | 3/1995 | Tews et al. .................. 324/634 |
| 5,666,061 A | | 9/1997 | Assenheim |
| 6,050,946 A | * | 4/2000 | Teo ............................ 600/443 |
| 6,347,286 B1 | * | 2/2002 | Petillon ....................... 702/77 |
| 6,389,365 B1 | * | 5/2002 | Boyan et al. .................. 702/76 |
| 6,653,799 B2 | * | 11/2003 | Cammack .................... 315/224 |
| 6,686,870 B2 | * | 2/2004 | Nishimura et al. ............ 342/70 |
| 2003/0076118 A1 | * | 4/2003 | Adams et al. ............... 324/664 |

\* cited by examiner

FOREIGN PATENT DOCUMENTS

DE 199 34 881 1/2001

OTHER PUBLICATIONS

John Clayton Rawlins, Basic AC Circuits, 2000, Newnes, Edition 2, p. 464, ISBN 0750671734.*

*Primary Examiner*—Eliseo Ramos Feliciano
*Assistant Examiner*—Ricky Ngon
(74) *Attorney, Agent, or Firm*—Jordan and Hamburg LLP

(57) ABSTRACT

The invention relates to a method for determining the humidity and/or density of a dielectric material in a resonator that is filled with said material and that contains a transmitter and a receiver. According to said method: the transmitter emits a signal; a resonance curve of the filled resonator is scanned in stages, whereby respective signal intensity values ($U_i$) are measured at different frequencies ($f_i$); the resonant frequency ($f_{rm}$) and the bandwidth ($BW_m$) are determined for the filled resonator from measured points ($f_i/U_i$); and the humidity ($\psi$) and/or density ($\rho$) of the material are calculated by solving a second system of equations (G2), containing the resonant frequencies ($f_{r0}$, $f_{rm}$) and bandwidths ($BW_0$, $BW_m$) of the empty and filled resonators and known calibration coefficients ($a_{r1}$, $a_{r2}$, $b_{r1}$, $b_{r2}$, $c_{r1}$, $c_{r2}$, $a_{bw1}$, $a_{be2}$, $b_{bw1}$, $b_{bw2}$, $c_{bw1}$, $c_{bw2}$) of said resonator. The aim of the invention is to provide a method for determining the humidity independently of the density in a rapid, precise manner.

8 Claims, 2 Drawing Sheets

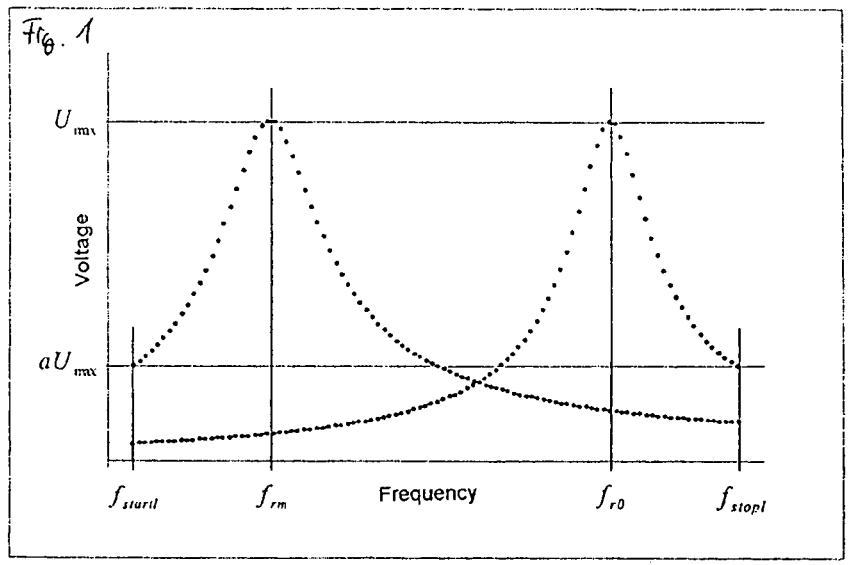
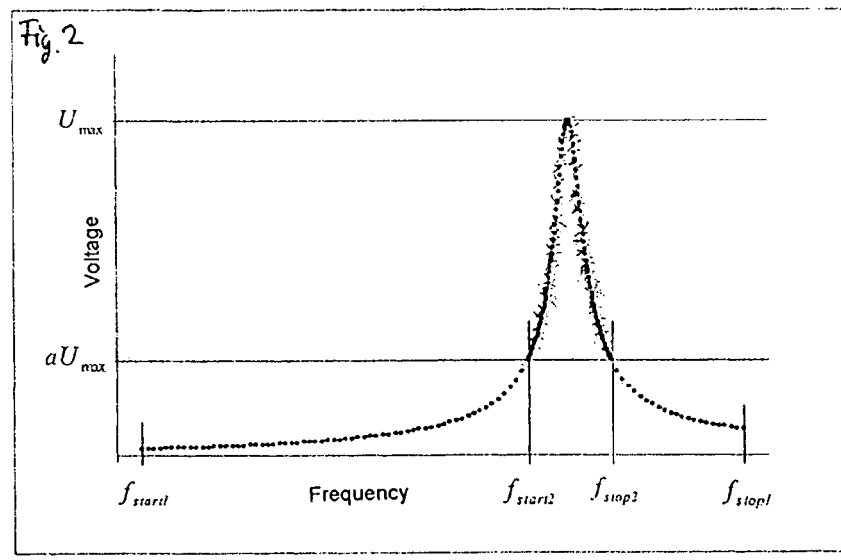
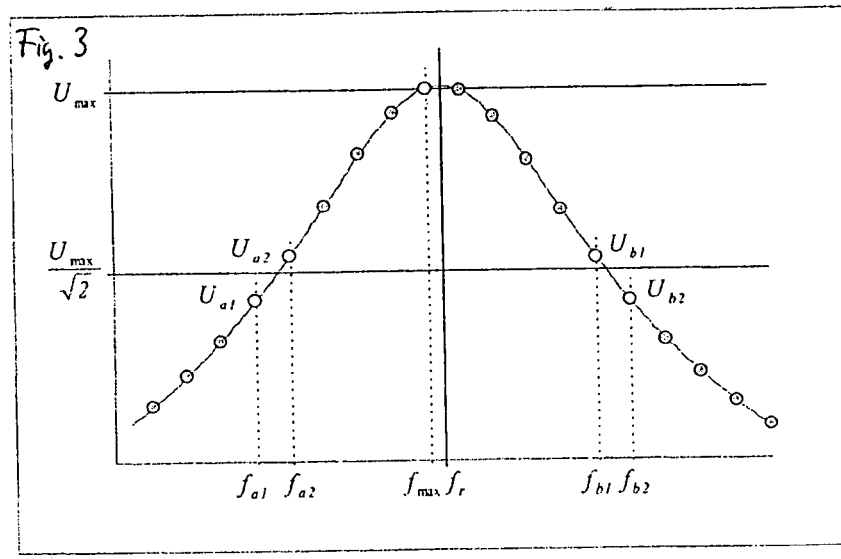

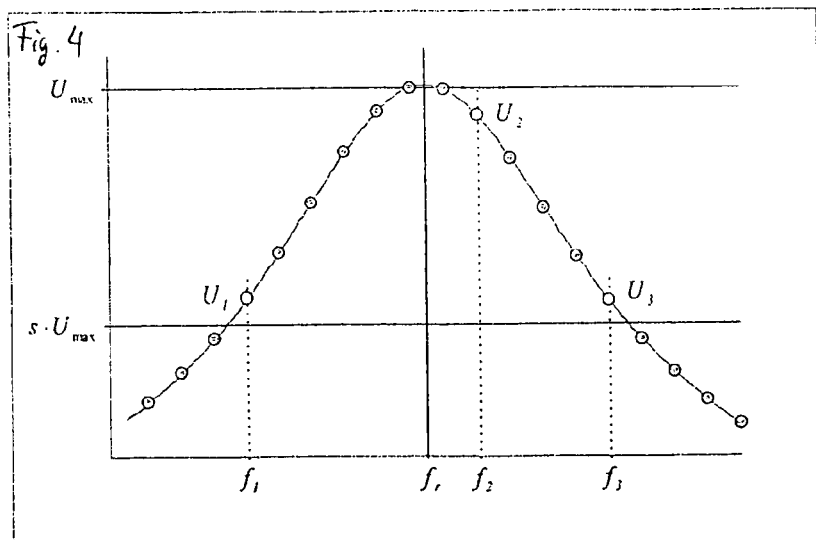
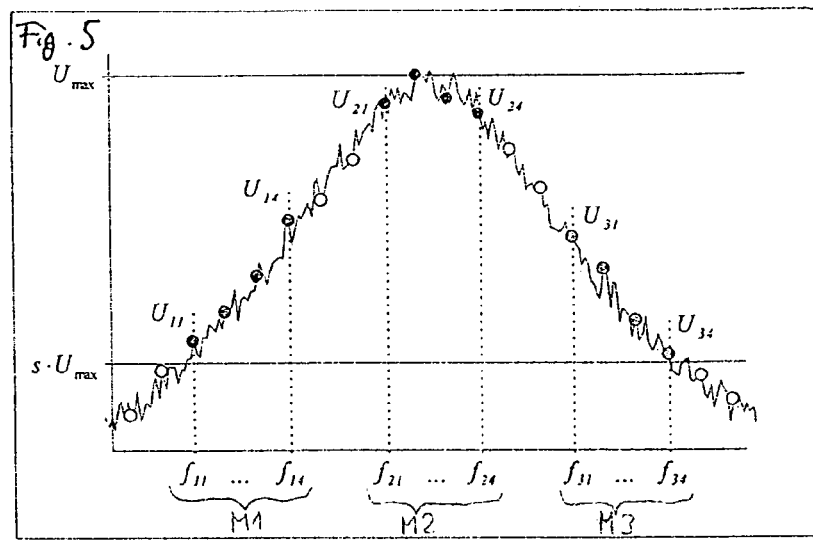
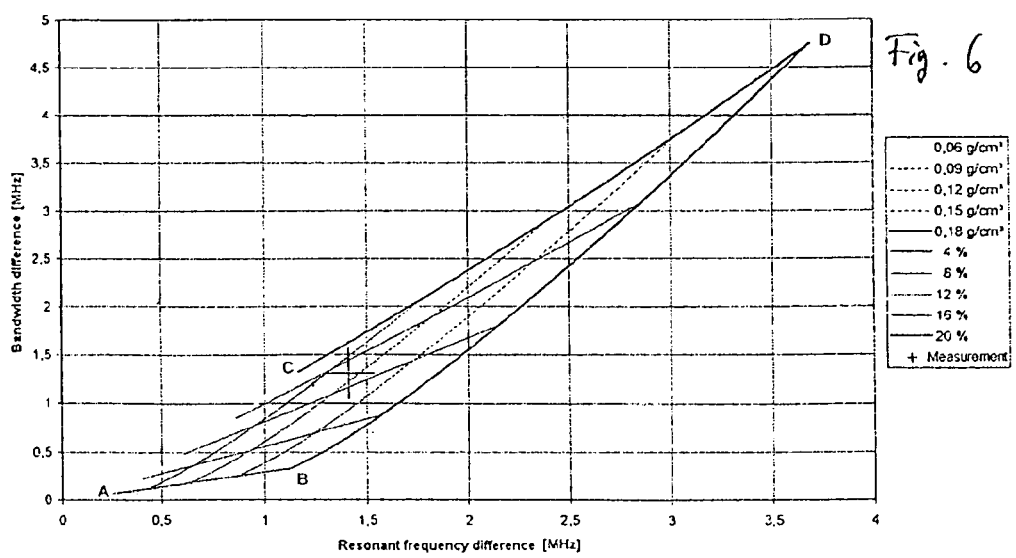

METHOD FOR DETERMINING THE HUMIDITY AND DENSITY OF A DIELECTRIC MATERIAL

BACKGROUND OF THE INVENTION

The invention relates to a method for determining the humidity and/or density of a dielectric material in a resonator filled with the material, comprising a sender and a receiver.

The dielectric properties of a material, described by the complex relative dielectric constant $\in_r = \in'_r - i\in''_r$, can be affected by humidity and density in case of porous materials. Humidity and density thus modify the scalar parameters resonant frequency $f_r$ and resonator quality Q of a material-filled resonator in contrast to those of the empty, air-filled resonator ($f_{r_0}$ and $Q_0$) in such a way that $$f_{r_m} = \frac{f_{r_0}}{\sqrt{\varepsilon_r}} \text{ and } \frac{1}{Q_m} = \frac{1}{Q_0} + \frac{\varepsilon''_r}{\varepsilon'_r},$$

wherein $1 \leq \in'_r \leq \in'_{r_{max}}$ and $0 \leq \in''_r \leq \in''_{r_{max}}$, wherein $\in'_{r_{max}}$ and $\in''_{r_{max}}$ are the maximum values resulting for the respective material from the assigned humidity range and density range.

In prior art, different methods are known for measuring the humidity or density of granular materials, in which the resonance behavior of a matter-filled resonator is used.

For example, from U.S. Pat. No. 5,666,061 a method is known for measuring the humidity in granular materials by means of microwaves. There, one electronically reacts to a threshold while bidirectionally sweeping a frequency range. From the chronological properties of pulses created in such a way the components of the dielectric constant are deduced.

All methods are relatively slow and have either a dependency of the density of the material or have relatively large errors in the determination of the humidity.

The invention is underlied by the problem to specify a method of the type initially mentioned, by which a fast, accurate and density-independent determination of the humidity is possible.

SUMMARY OF THE INVENTION

For the purpose of the invention, any arbitrary quantity describing the resonance width can be considered as a bandwidth in the following, wherein appropriate adjustments have to be provided in the respective definitions, in particular of the threshold values, and equations.

By digitally recording the resonance curve, a fast acquisition of the measuring values is possible. Thus, a close chronological-spatial assignment of the humidity determined from these values to material dynamically guided through the resonator is possible. For this purpose, the invention provides for that the sender emits a signal; a resonance curve of the filled resonator is swept, wherein respective related signal strength values of the receiver signal are measured at different frequencies; the resonant frequency and the bandwidth are determined for the filled resonator from the measured points; and the humidity and/or density of the material is calculated by solving a second system of equations comprising the resonant frequencies and the bandwidths of the empty and of the filled resonator and known calibration coefficients of the resonator. This method enables a density-independent determination of the humidity of the material. Besides, the density of the material can be acquired with little effort.

A preferred embodiment provides for that, from the points for determining the bandwidth of the filled resonator, either the quantities resonant frequency, resonator quality and resonance maximum are determined and the bandwidth is calculated therefrom, or cut-off frequencies are determined and the resonant frequency and the bandwidth are calculated therefrom.

In another embodiment a lower threshold value is calculated and a second sweeping pass with smaller step sizes is performed in that range in which the signal strength values are higher than the threshold value. By a two-pass procedure the accuracy can be significantly increased and, nevertheless, the required time can be kept short, in particular if, during the second sweeping pass, a decreased step size is used in a range of the resonance peak only.

Advantageously, sweeping the resonance curve is performed in equally spaced steps. The simplest and fastest form of sweeping consists of equally spaced steps. Variable step sizes in the second sweeping pass can shorten its duration.

Preferably, the sender is operated using a constant strength. The measuring values at the receiver can be used without adjusting or scaling them in case of a constant signal strength.

In a possible embodiment, the cut-off frequencies of the resonator are determined by determining the point having the highest receiver signal strength value, and, starting from this point, calculating a threshold value; determining two respective proximate points for positive and negative slope sections, the signal strength values of these points lying below and above the threshold value; calculating first and second cut-off frequencies therefrom by respectively interpolating between the proximate points. Determining the cut-off frequencies by interpolating between point pairs surrounding a threshold value as an initial parameter for determining the humidity and/or density is a fast and simple method.

An advantageous embodiment thereby provides for that the threshold value corresponds to an attenuation of 3 dB in relation to the highest signal value. If the threshold value is chosen corresponding to an attenuation of 3 dB, starting from the maximum signal strength value, the equations to be solved obtain a very simple form.

In an alternative embodiment the quantities resonant frequency, resonator quality and resonance maximum of the resonator are determined by arbitrarily and/or randomly selecting three points and solving a first system of equations for these quantities, the system consisting of three equations of an analytic resonance curve that are valid for the three points. The resonant frequency, the resonator quality and the resonance amplitude can be directly determined as the initial parameters for determining the humidity and/or density even faster and with less error than by interpolation by solving a first system of equations consisting of three equations and thus being completely determined, wherein for each point out of a group of three one of the three equations is valid, the three points being selected from the present set. In particular, noisy resonance curves can be analyzed more exactly this way.

In another alternative embodiment the quantities resonant frequency, resonator quality, resonance maximum of the resonator are determined by arbitrarily and/or randomly selecting a set of points whose number is an integer multiple of three and at least six, and splitting up the point set into three equally sized groups; for each combination of three points, wherein each point comes from a different group, solving a first system of equations for these quantities, the system consisting of three equations of the analytic resonance curve valid for these three points; and creating the average for each quantity from the values calculated at the combinations. Even more exact values than with three points can be obtained by creating several triple-groups from the present point set and averaging the initial parameters obtained thereby over all groups.

In an advantageous embodiment, as a condition for arbitrarily and/or randomly selecting the points, the signal value of a point to be selected is higher than the highest signal value attenuated by 3 dB. In both procedures using three points or a multiple thereof, preferably only those points from the resonance curve are selected whose signal strength is higher than the maximum value of all measurement values, attenuated by 3 dB, as this way only significant values are used.

The system of equations to be solved is preferably chosen in such a way that it describes, in a good approximation, the correlation of humidity and density with a variation of resonant frequency and resonator quality or, respectively, with a variation of resonant frequency and bandwidth.

Advantageously the second system of equations is non-linear.

In a preferred embodiment the sweeping by means of the sender is performed up to the microwave area.

Advantageously, voltage values or current values of the receiver are used for measuring the receiver signal. Preferably, the electrical voltage rising at the receiver serves for acquiring the resonance curve, because it is measurable easily and without back coupling. However, the current in a receiver circuit can be measured, too.

In the following, the denomination $U_i$ is used for the measured quantities. However, in doing so, it shall not be implied to use the voltage only.

The resonance curve to be reconstructed from the discrete measuring points is an approximation as-good-as-possible to the real resonance curve only. It is characterized by the course of the signal amplitude U at the receiver against the supplied frequency f, wherein $U_r$ is the resonance maximum and Q is the quality of the resonance:

$$U = \frac{U_r}{\sqrt{1 + Q^2 \left( \frac{f}{f_r} - \frac{f_r}{f} \right)^2}}$$

The cut-off frequencies $f_a$ and $f_b$ are those frequencies at which the signal strength exceeds and falls below a defined value, respectively. For this purpose, preferably the value corresponding to an attenuation of the maximum by 3 dB is chosen: $U_a = U_b = U_r/\sqrt{2}$. Between the cut-off frequencies and the curve parameters resonant frequency $f_r$ and resonator quality Q there are the correlations:

$$f_r = \sqrt{f_a \cdot f_b}, Q = \frac{\sqrt{f_a \cdot f_b}}{f_b - f_a}.$$

The distance between the cut-off frequencies is defined as the bandwidth $$BW = f_b - f_a = \frac{f_r}{Q}.$$

In the following, the invention is described in further detail using examples of embodiments.

BRIEF DESCRIPTION OF THE DRAWINGS

FIG. 1 shows a sweeped resonance curve;

FIG. 2 shows a resonance curve sweeped in a two-pass procedure;

FIG. 3 shows a first way for determining the resonance parameters;

FIG. 4 shows a second way for determining the resonance parameters;

FIG. 5 shows a third way for determining the resonance parameters; and

FIG. 6 shows a two-dimensional representation of calibration curves.

DETAILED DESCRIPTION OF THE INVENTION

In FIG. 1, two resonance curves are depicted above each other like they have been recorded using the method according to the invention; the right resonance curve at an empty, the left resonance curve at a material-filled resonator.

By sweeping (wobbling) the resonator between the start frequency $f_{start1}$ and the stop frequency $f_{stop1}$, the resonance curve is acquired in discrete steps. The start frequency is calculated from the maximally shifted frequency $$f_{r_m} = \frac{f_{r_0}}{\sqrt{\varepsilon_{r_{max}}}},$$

the maximally changed quality $$\frac{1}{Q_m} = \frac{1}{Q_0} + \varepsilon''_{r_{max}}$$

and the normalized voltage ratio $$a = \frac{U_a}{U_{max}} < \frac{1}{\sqrt{2}} : f_{start1} = -\frac{f_{r_m}}{2Q_m} \sqrt{\frac{1-a^2}{a^2}} + \sqrt{\left(\frac{f_{r_m}}{2Q_m}\right)^2 \cdot \frac{1-a^2}{a^2} + f_{r_m}^2}.$$

The stop frequency, using $f_r = f_{r_0}$, results as:

$$f_{stop1} = -\frac{f_{r_0}}{2Q_m} \sqrt{\frac{1-a^2}{a^2}} + \sqrt{\left(\frac{f_{r_0}}{2Q_m}\right)^2 \cdot \frac{1-a^2}{a^2} + f_{r_0}^2}.$$

The sweeping speed depends, among others, on the number $n_1$ of sweeping points and can be increased by a two-pass procedure as depicted in FIG. 2. For this purpose, first a sweeping is performed using a smaller number of sweeping points and, hence, a larger frequency step size $$\Delta f_1 = \frac{f_{stop1} - f_{start1}}{n_1 - 1}$$

and, in a second iteration, after previously determining the start and stop frequencies $f_{start2}=f|U\approx U_a$ $_{\Delta f>0}$, $f_{stop2}=f|U\approx U_a$ $_{\Delta f<0}$ or $f_{start2}=f|U\approx U_a$ $_{\Delta U<Ur}$, $f_{stop2}=f|_{U\sim Ua}\Delta U>Ur$, another sweeping is subsequently performed using a smaller frequency step size $$\Delta f_2 = \frac{f_{stop2} - f_{start2}}{n_2 - 1}$$

between these frequencies.

From the sweeped, measured resonance curve the resonator parameters $f_r$, Q and $U_r$ can be determined, for example, according to the fafb procedure, the three-points procedure or the 3k-points procedure. Other procedures are possible, too.

FIG. 3 shows the fafb procedure. It is based on directly determining a first and a second cut-off frequency $f_a$, $f_b$ from the measured resonance curve. For this purpose, first the point (also called sweeping point) ($f=f_{max}/U=U_{max}$) having the highest voltage $U=U_{max}$ is determined for calculating a 3 dB threshold line $$U_{3dB} = \frac{U_{max}}{\sqrt{2}}.$$

Subsequently, the respective two points in the immediate proximity of the 3 dB threshold line are determined. By linearly interpolating between the sweeping points a1 and a2 as well as b1 and b2 the first and the second 3 dB cut-off frequency $f_a$, $f_b$ are obtained:

$$f_a = f_{a1} + \frac{\frac{U_{max}}{\sqrt{2}} - U_{a1}}{U_{a2} - U_{a1}}(f_{a2} - f_{a1}),$$

$$f_b = f_{b1} + \frac{\frac{U_{max}}{\sqrt{2}} - U_{b1}}{U_{b2} - U_{b1}}(f_{b2} - f_{b1}).$$

From the equations $$f_r = \sqrt{f_a \cdot f_b}, Q = \frac{\sqrt{f_a \cdot f_b}}{f_b - f_a},$$

$f_r$ and Q can be calculated. The resonance voltage $U_r$ then results as:

$$U_r = U_{max} \cdot \sqrt{1 + Q^2\left(\frac{f_{max}}{f_r} - \frac{f_r}{f_{max}}\right)^2}.$$

Calculating the cut-off frequencies is more or less error-prone because of the discretization of the resonance curve—on one hand, by the determination of the 3 dB threshold line ($U_a=U_{max}/\sqrt{2}\leq U_r/\sqrt{2}$) derived from $U_{max}$ and, on the other hand, by the linear interpolation between the sweeping points a1, a2, b1, b2. A higher sweeping rate indeed reduces the errors, but also increases the sweeping time and thus reduces the sweeping speed. At best, a non-linear interpolation is possible in this procedure in order to improve accuracy.

In the three-points procedure shown in FIG. 4, three sweeping points $U_1$, $U_2$, $U_3$ are selected arbitrarily or by a random generator preferably above the line $U_s=s\cdot U_{max}$ with $$s < \frac{1}{\sqrt{2}}.$$

By solving the first system of equations G1:

$$U_1 = \frac{U_r}{\sqrt{1 + Q^2\left(\frac{f_1}{f_r} - \frac{f_r}{f_1}\right)^2}}, U_2 = \frac{U_2}{\sqrt{1 + Q^2\left(\frac{f_2}{f_r} - \frac{f_r}{f_2}\right)^2}},$$

$$U_3 = \frac{U_3}{\sqrt{1 + Q^2\left(\frac{f_3}{f_r} - \frac{f_r}{f_3}\right)^2}}$$

the resonator parameters $f_r$, Q and $U_r$ are obtained:

$$f_r = \sqrt[4]{\frac{U_1^2(U_3^2-U_2^2)f_1^2 + U_2^2(U_1^2-U_3^2)f_2^2 + U_3^2(U_2^2-U_1^2)f_3^2}{\frac{U_1^2(U_2^2-U_3^2)}{f_1^2} + \frac{U_2^2(U_3^2-U_1^2)}{f_2^2} + \frac{U_3^2(U_1^2-U_2^2)}{f_3^2}}}$$

$$Q = \sqrt{\frac{U_1^2 - U_2^2}{U_2^2\left(\frac{f_2}{f_r} - \frac{f_r}{f_2}\right)^2 - U_1^2\left(\frac{f_1}{f_r} - \frac{f_r}{f_1}\right)^2}}$$

$$U_r = U_1\sqrt{1 + Q^2\left(\frac{f_1}{f_r} - \frac{f_r}{f_1}\right)^2}$$

The advantage of the three-points procedure in relation to the fafb procedure lies in that no errors occur because of the discretization of the resonance curve, and that only few points are needed for sweeping the resonance curve, and thus a high sweeping speed is achieved.

If the resonance curve is noisy, error-prone resonator parameters are determined by the three-points procedure, too. In order to reduce the impact of the noise, more than three sweeping points are selected, namely a number 3·k, k=2, 3, 4, . . ., and are split up into three groups M1, M2, M3, having k points per group above the line $U_s=s\cdot U_{max}$. FIG. 5 shows this 3k-points procedure. For all $k^3$ possibilities of combining one respective point from each of the three groups, the resonator parameters are determined from the first system of equations G1 according to the three-points procedure described above, and the $k^3$ partial results are averaged subsequently:

$$f_r = \frac{1}{k^3}\sum_{j=1}^{k^3} f_{rj}, Q = \frac{1}{k^3}\sum_{j=1}^{k^3} Q_j, U_r = \frac{1}{k^3}\sum_{j=1}^{k^3} U_{rj}.$$

In order to determine humidity and density from determined resonator parameters, the used arrangement is calibrated using material of known humidity and density. The calibration is advantageously performed out of the regular operation.

In the calibration, the electrical resonator values resonant frequency $f_r$, resonator quality Q and bandwidth BW(BW=$f_r$/Q) are respectively assigned to the material quantities humidity $\psi$ and density $\rho$. This assignment between the material values and the electrical values is non-linear and can be described for a defined range of humidity and density with sufficient accuracy, for example, by the following second system of equations G2:

$$\Delta f_r = a_{f_r2}\rho^2\psi^2 + a_{f_r1}\rho\psi^2 + b_{f_r2}\rho^2\psi + b_{f_r1}\rho\psi + c_{f_r2}\rho^2 + c_{f_r1}\rho$$

$$\Delta BW = a_{BW_2}\rho^2\psi^2 + a_{BW_1}\rho\psi^2 + b_{BW_2}\rho^2\psi + b_{BW_1}\rho\psi + c_{BW_2}\rho^2 + c_{BW_1}\rho$$

$\Delta f_r$ and $\Delta BW$ are the differences of resonant frequency and bandwidth, respectively, between the empty and the material-filled resonator:

$$\Delta f_r = f_{r_0} - f_{r_m}, \Delta BW = BW_m - BW_0$$

Now, it is an object of the calibration to determine the twelve calibration coefficients $a_{f_r1}$, $a_{f_r2}$, $b_{f_r1}$, $b_{f_r2}$, $c_{f_r1}$, $c_{f_r2}$, $a_{BW_2}$, $a_{BW_1}$, $b_{BW_1}$, $b_{BW_2}$, $c_{BW_1}$, $c_{BW_2}$ for the respective material from a sufficient large number of calibration values ($\Delta f_r$ and $\Delta BW$ with related material values $\psi$ und $\rho$).

For this purpose, the measuring values of the resonant frequency difference $\Delta f_r$ and the bandwidth difference $\Delta BW$ are assigned to the humidity and density values that have been determined by appropriate reference methods. These calibration values characterizing the resonant frequency and bandwidth depending on humidity and density are the basis for determining the calibration coefficients. The regression of the calibration values of equal humidity is performed in the form of $\Delta f_r = d_{f_r2}\rho^2 + d_{f_r1}\rho$ and $\Delta f_r = d_{BW_2}\rho^2 + d_{BW_1}\rho$, wherein the regression curves have to run through the origin, as $\Delta f_r$ and $\Delta BW$ are zero for the empty resonator (air having $\rho$=0). The regression provides calibration points of equal density depending on the humidity. Using these, another regression of the form $\Delta f_r = a_{f_r}\psi^2 + b_{f_r}\psi + c_{f_r}$ and $\Delta BW = a_{BW}\psi^2 + b_{BW}\psi + c_{BW}$ is performed. The values determined this way for the regression coefficients $a_{f_r}$, $b_{f_r}$, $c_{f_r}$ and $a_{BW}$, $b_{BW}$, $c_{BW}$ are plotted against the density and, therefrom, the calibration coefficients are determined by a quadratic regression.

FIG. 6 shows the results of the calibration in the form of a set of curves which also serves for analysis.

From the measured resonant frequency difference values $\Delta f_r$ and bandwidth difference values $\Delta BW$ humidity content $\psi$ and density $\rho$ are calculated for the respective material by solving the above second system of equations G2.

In doing so, two real and two imaginary roots result. From the course of the calibration curves in the $\Delta f_r$,$\Delta BW$ diagram it can be determined if there is only one real solution in the humidity and density range of interest. In the $\Delta f_r$,$\Delta BW$ diagram the bandwidth difference is represented in dependency of the resonant frequency difference for curves of equal density and humidity. If the course of these curves, characterized by the points A, B, C und D in FIG. 6, is continuous and unique in the humidity and density range of interest then only one real solution exists in this range.

For solving the second system of equations G2 an iterative procedure is appropriate. For this purpose, the second system of equations G2 is solved for $\psi$:

$$\psi = -\frac{b_{f_r2}\rho + b_{f_r1}}{2a_{f_r2}\rho + 2a_{f_r1}\rho} + \sqrt{\left(\frac{b_{f_r2}\rho + b_{f_r1}}{2a_{f_r2}\rho + 2a_{f_r1}\rho}\right)^2 - \frac{c_{f_r2}\rho^2 + c_{f_r1}\rho - \Delta f_{r_0}}{a_{f_r2}\rho^2 + a_{f_r1}\rho}}$$

-continued $$\psi = -\frac{b_{BW_2}\rho + b_{BW_1}}{2a_{BW_2}\rho + 2a_{BW_1}\rho} + \sqrt{\left(\frac{b_{BW_2}\rho + b_{BW_1}}{2a_{BW_2}\rho + 2a_{BW_1}\rho}\right)^2 - \frac{c_{BW_2}\rho^2 + c_{BW_1}\rho - \Delta BW_0}{a_{BW_2}\rho^2 + a_{BW_1}\rho}}$$

From the intersection of both equations in a humidity-density diagram the sought values for $\psi$ and $\rho$ are obtained.

LIST OF REFERENCE NUMERALS $f_r$ Resonant frequency in the general case
$f_{r_0}$ Resonant frequency of the empty resonator
$f_{r_m}$ Resonant frequency of the filled resonator
$f_{start1}$, $f_{stop1}$ Start and stop frequencies for first sweeping pass
$U_{max}$ Highest signal strength value measured
a, s Threshold value factors
$f_{start2}$, $f_{stop2}$ Start and stop frequencies for second sweeping pass
$f_{max}$ Frequency at which the highest signal strength value is present
($f_{a1}$/$U_{a1}$), ($f_{a2}$/$U_{a2}$) Proximate points of the first cut-off frequency
($f_{b1}$/$U_{b1}$), ($f_{b2}$/$U_{b2}$) Proximate points of the second cut-off frequency
($f_1$/$U_1$) ... ($f_3$/$U_3$) Three selected points
M1, M2, M3 point groups
($f_{11}$/$U_{11}$) ... ($f_{14}$/$U_{14}$) Elements of point group M1
($f_{21}$/$U_{21}$) ... ($f_{24}$/$U_{24}$) Elements of point group M2
($f_{31}$/$U_{31}$) ... ($f_{34}$/$U_{34}$) Elements of point group M3
A,B,C,D Limits of the humidity and density range of interest

The invention claimed is:

1. A method for determining the humidity and/or density of a dielectric material in a resonator filled with the material, the resonator including a sender and a receiver, the method comprising:
    emitting a signal by the sender;
    sweeping a resonance curve of the filled resonator;
    measuring appropriate signal strength values of the receiver signal at respective different frequencies;
    determining a resonant frequency and a bandwidth for the filled resonator from points corresponding to the signal strength values of the receiver signal at the respective different frequencies measured; and
    calculating at least one of humidity or density of the material by solving a second system of equations comprising the resonant frequencies and respective bandwidths of the empty and of the filled resonator and known calibration coefficients of the resonator, wherein, from the points for determining the bandwidth of the filled resonator, cut-off frequencies are determined and the resonant frequency and the bandwidth are calculated therefrom, and wherein the cut-off frequencies of the resonator are determined by:
        determining a one of the points having a highest signal strength value, and, starting from said one of the points, calculating a threshold value;
        determining two proximate points for positive and negative slope sections, the signal values of said two proximate points lying below and above the threshold value, respectively; and
        calculating first and second cut-off frequencies therefrom by respectively interpolating between the two proximate points.

2. The method according to claim 1, wherein the threshold value corresponds to an attenuation of 3 dB in relation to the highest signal strength value.

3. A method for determining the humidity and/or density of a dielectric material in a resonator filled with the material, the resonator including a sender and a receiver, the method comprising:

emitting a signal by the sender;

sweeping a resonance curve of the filled resonator;

measuring appropriate signal strength values of the receiver signal at respective different frequencies;

determining a resonant frequency and a bandwidth for the filled resonator from points corresponding to the signal strength values of the receiver signal at the respective different frequencies measured; and calculating at least one of humidity or density of the material by solving a second system of equations comprising the resonant frequencies and respective bandwidths of the empty and of the filled resonator and known calibration coefficients of the resonator, wherein, from the points for determining the bandwidth of the filled resonator, the quantities resonant frequency, resonator quality and resonance maximum are determined and the bandwidth is calculated therefrom, and wherein the quantities resonant frequency, resonator quality, and resonance maximum of the resonator are determined by:

at least one of arbitrarily or randomly selecting a set of the points for which a number is an integer multiple of three and is at least six, and splitting up the point set into three equally sized groups;

for each combination of three points, wherein each point comes from a different one of the groups, solving a first system of equations to obtain resonant parameters, the system consisting of three equations of the analytic resonance curve valid for said three points; and for each of the resonant parameters, creating an average of values calculated at said combinations.

4. The method according to claim 3, wherein, as a condition for the at least one of arbitrarily or randomly selecting the points, the signal value of a particular one of the points to be selected is higher than the highest signal value attenuated by 3 dB.

5. The method according to claim 1 or 3, wherein the second system of equations describes, as at least an approximation, the correlation of humidity and density with the variation of resonant frequency and resonator quality, or with the variation of resonant frequency and bandwidth, in a predefined range of humidity and density.

6. The method according to claim 1 or 3, wherein the second system of equations is non-linear.

7. The method according to claim 1 or 3, wherein the sweeping by the sender is performed up to the microwave area.

8. The method according to claim 1 or 3, wherein voltage values or current values of the receiver are used for measuring the receiver signal.

* * * * *